United States Patent [19]

Fry

[11] 4,428,863

[45] Jan. 31, 1984

[54] ALUMINA COMPOSITIONS OF IMPROVED STRENGTH USEFUL AS CATALYST SUPPORTS

[75] Inventor: William E. Fry, Angleton, Tex.

[73] Assignee: The Dow Chemical Company, Midland, Mich.

[21] Appl. No.: 395,560

[22] Filed: Jul. 6, 1982

[51] Int. Cl.$^3$ .......................... B01J 21/04; B01J 23/54
[52] U.S. Cl. ............................ 502/8; 502/159; 502/263; 502/348; 502/355
[58] Field of Search ........................ 252/463, 455 R

[56] References Cited

U.S. PATENT DOCUMENTS

| | | | |
|---|---|---|---|
| 2,499,675 | 3/1950 | Owen | 252/465 |
| 2,950,169 | 8/1960 | Murray et al. | 23/143 |
| 2,984,630 | 5/1961 | Braithwaite | 252/464 |
| 3,172,866 | 3/1965 | Belon | 252/463 |
| 3,172,893 | 3/1965 | Ameen | 252/463 |
| 3,222,129 | 12/1965 | Osment et al. | 23/141 |
| 3,223,483 | 12/1965 | Osment | 23/143 |
| 3,226,191 | 12/1965 | Osment et al. | 23/141 |
| 3,461,140 | 8/1969 | Titzenthaler | 252/463 |
| 3,501,417 | 3/1970 | De Maio | 252/455 R |
| 3,628,914 | 12/1971 | Graulier | 23/143 |
| 3,664,970 | 5/1972 | De Maio | 252/454 |
| 3,779,946 | 12/1973 | Dorn et al. | 252/455 R |
| 3,804,781 | 4/1974 | Colgan | 252/463 |
| 3,856,708 | 12/1974 | Carithers | 252/463 |
| 3,907,512 | 9/1975 | Ziegenhain et al. | 23/293 A |
| 3,907,982 | 9/1975 | Leach | 423/630 |
| 3,928,236 | 12/1975 | Rigge et al. | 252/463 |
| 3,987,155 | 10/1976 | Ziegenhain | 423/628 |
| 3,997,476 | 12/1976 | Cull | 252/463 |
| 4,001,144 | 1/1977 | Pearson et al. | 252/463 |
| 4,022,715 | 5/1977 | Bornfriend | 252/463 |
| 4,039,481 | 8/1977 | Kimura et al. | 252/464 |
| 4,098,874 | 7/1978 | Mitsche et al. | 423/628 |
| 4,212,771 | 7/1980 | Hamner | 252/463 |
| 4,224,302 | 9/1980 | Okamoto et al. | 252/463 |
| 4,242,233 | 12/1980 | Ball et al. | 252/431 N |
| 4,369,131 | 1/1983 | Risch et al. | 252/455 R |

FOREIGN PATENT DOCUMENTS 2402094  4/1975  Fed. Rep. of Germany ...... 252/463

OTHER PUBLICATIONS

Chem. Abst. 78:38236b–"Preparation and Properties of a Barium Silicate–Alumina Cement", Kulikova et al.
Chem. Abst. 88:66352q–"Thermostable Alumina Used as a Catalyst Carrier", Janiak et al.
Chem. Abst. 88:54334x–"Binder Mixture Based on Barium Aluminate", Gessner et al.

*Primary Examiner*—Delbert E. Gantz
*Assistant Examiner*—Lance Johnson
*Attorney, Agent, or Firm*—A. C. Ancona

[57] ABSTRACT

A process of making a high purity, low surface area porous alumina support having improved crush strength and abrasion resistance which comprises employing with the alumina a small amount of barium aluminate or silicate during its manufacture.

13 Claims, No Drawings

ALUMINA COMPOSITIONS OF IMPROVED STRENGTH USEFUL AS CATALYST SUPPORTS

BACKGROUND OF THE INVENTION

Aluminas and alumina-silicates are well known to be useful as catalysts, adsorbents and catalyst supports. These materials are made by fusing high purity (99+%) aluminum oxide with or without silica (usually as sodium silicate). They may be very porous or non-porous and have a high or low surface area depending upon the use to be made of them. When used as a catalyst the support may comprise any porous, inert material which does not detrimentally influence the catalytic reaction wherein it is employed. An early patent describing a method of making a pelleted alumina catalyst is U.S. Pat. No. 2,499,675.

Representative of the method of making such supports is the following description found in U.S. Pat. No. 3,664,970. The particular support therein is said to be useful as a support for a silver catalyst employed in the oxidation of ethylene to ethylene oxide. For this purpose the support material comprises 90 percent or more by weight alpha alumina and 1 to 6 percent by weight silica. A preferred support material comprises 90 percent or more by weight alpha alumina, 1 to 6 percent by weight silica and 0.1 to 0.4 percent by weight baryta.

The high-purity aluminum oxide preferably in the alpha alumina phase, is throughly mixed with temporary and permanent binders. The temporary binders are thermally decomposable organic compounds of moderate to high molecular weight (i.e., molecular weights above about 250) and, on decomposition, produce the pore structure of the support. The permanent binders are inorganic clay-type materials having fusion temperatures below that of the alumina and are responsible for imparting mechanical strength to the finished support. Silica and baryta can also be added in quantity sufficient to obtain a finished support of the desired composition. After thorough dry-mixing, sufficient water is added to the mass to form the mass into a paste-like substance. The catalyst support particles are then formed from the paste by conventional means such as, for example, high pressure extrusion, granulation or other ceramic forming processes. The particles are then dried and are subsequently fired at an elevated temperature which is in the range of 1,200° to 1,600° C.

In the firing step, the temporary binders are thermally decomposed to carbon dioxide and water and are volatilized, leaving voids in the support mass. These voids are the genesis of the pore structure of the finished support. Suitable temporary binders include such materials as the celluloses and substituted celluloses, e.g. cellulose itself, methylcellulose, ethylcellulose, and carboxyethylcellulose, stearates such as organic stearate esters, e.g. methyl or ethyl stearate, waxes and the like. As firing is continued, the temperature reaches the point at which the permanent binder (inorganic clay such as the kaolins or the ball clays) fuses. The catalyst support is then permitted to cool and, during cooling, the permanent binder sets and acts as a cement to bond the catalyst support particles and thereby impart mechanical strength to the support and ensure maintenance of the pore structure.

Catalyst supports of desired characteristics can be readily produced by the foregoing procedure. Control of pore size, pore size distribution and porosity are readily affected by appropriate adjustment in known manner of the size of the starting alumina particles, and of the particle size and concentration of the temporary and of the permanent binders in the starting mix. The larger the starting alumina particle size, the greater will be the porosity of the finished catalyst. The more homogeneous in size are the alumina particles, the more uniform will be the pore structure. Similarly, increasing the concentration of the temporary binder will also increase the overall porosity of the finished catalyst support.

Earlier patents which describe the making of alumina supports are U.S. Pat. Nos. 2,499,675; 2,950,169 and 3,172,866. Other patents such as U.S. Pat. Nos. 3,222,129; 3,223,483 and 3,226,191 show the preparation of active aluminas. A particular alumina pellet having high mechanical strength is described in U.S. Pat. No. 3,628,914. Methods of making highly porous aluminas are disclosed in U.S. Pat. Nos. 3,804,781; 3,856,708; 3,907,512 and 3,907,982. Alumina carriers having high thermal stability are disclosed in U.S. Pat. No. 3,928,236. Other more recent improvements in making catalyst carriers are found in U.S. Pat. Nos. 3,987,155; 3,997,476; 4,001,144; 4,022,715; 4,039,481; 4,098,874 and 4,242,233.

High purity alumina is desired in order to avoid any extraneous elements, e.g. sodium, which might deleteriously affect the catalytic coating. This is especially true for those supports used to make silver catalysts for use in making ethylene oxide. Such high purity supports have been made, but most do not have as good crush strength as do the lower purity supports. Those high strength, high purity supports which have been made have low porosity which is undesirable in supports for use in EO manufacture. Supports used for silver catalysts employed in the oxidation of ethylene to ethylene oxide also are desirably of low surface area, i.e. less than about 1 $m^2/g$. It would, therefore, be highly desirable to have high purity, high porosity, low surface area supports of increased strength for use in making silver catalysts for EO manufacture.

The present invention is the discovery that adding to the high purity alumina particular barium salts, i.e. the aluminate or silicate, shows an unexpected improvement in strength and abrasion resistance over the known manner of adding barium which is as the oxide, i.e. baryta, as indicated above. Although it is known (U.S. Pat. No. 2,984,630) to add sodium aluminate to alumina to make support materials, the barium aluminate previously has not been disclosed.

SUMMARY OF THE INVENTION

Barium aluminate and barium silicate each provide improved crush strength and abrasion resistance to the support when incorporated into the alumina as binders in making a high purity low surface area alumina binders in making a high purity low surface area alumina support. Sufficient of the barium compound is added to provide from about 0.1% to about 1.0% barium in the finished support.

DETAILED DESCRIPTION OF THE INVENTION

The high purity alumina support of the present invention which is useful as a carrier for silver is made from a high purity α-alumina 99.5% by weight $Al_2O_3$ containing about 0.08% $SiO_2$, about 0.04% $Fe_2O_3$ and about 0.2% volatile components. Water content can be up to 0.3%. While the above analysis of the high purity alumina is representative, the purity of the alumina may vary from about 98.9% to about 99.9% providing certain impurities, namely $Na_2O$, $SiO_2$ and $Fe_2O_3$ are kept below about 0.6, 0.2 and 0.05%, respectively.

To the high purity alumina is added from about 0.19% to about 1.9% of barium aluminate or from about 0.16% to about 1.6% of barium silicate, based on the total weight of alumina and barium compound together, with sufficient water to make a paste which can be molded or shaped into pellets or spheres. Ordinarily water is added in an amount of from about 8% to about 30% by weight based on the total weight of dry components, including additives, such as pore forming materials.

Other additives, e.g. an alkylated cellulose, can be used to affect the pore structure of the finished catalyst support. Such materials are methylcellulose, ethylcellulose, hydroxypropylmethylcellulose, hydroxybutylmethylcellulose, and the like. Other pore forming agents which can be substituted for the cellulosic materials are polyvinylalcohol, polyglycols, starches, gelatins, graphite, cereal grains, flour, plastics, e.g. polyethylene, organic ion exchange resins, and natural and synthetic fibers, e.g. cotton and polyester. They are added in amounts of from about 2% to about 20%. Since the barium aluminate and silicate act as binders for the alumina, no additional binders or cements ordinarily used by the art are necessary.

The paste-like material, having been formed into pellets or spheres, is fired at temperatures of from about 1200° C. to about 1700° C. for a period of time from about 0.5 to about 24 hours, the firing being done in an oxygen or air atmosphere. The temperature of firing is sufficiently high to fuse the alumina and barium salts without the addition of other binders normally used for that purpose. If desired, however, other known binders may be added providing no deleterious effect is obtained.

When such support is employed with a silver coating for the process of making ethylene oxide by the direct vapor phase oxidation of ethylene with oxygen or air, barium is usually added to the silver coating, either concurrently with the silver salt or prior or post added as a water soluble salt in order to prevent sintering of the silver during use. It was determined, however, that additional barium was not needed on the surface of the support in order to prevent the sintering of the silver coating.

Since barium oxide is known to have little anti-sintering effect when used as a component of the support, it was surprising to observe this effect when the barium was added as either the aluminate or silicate according to the present invention. In fact, it was even more surprising to find that, when the support material had barium incorporated according to the present invention, additional barium co-deposited on the surface of the support with the silver, e.g. as nitrate, usually had a deleterious effect on the activity and/or selectivity when used in the oxidation of ethylene to EO.

The following examples are representative of both the preparation of the support and its use as a support for silver in the manufacture of ethylene oxide.

A series of carriers was prepared from 325 mesh alumina powder. Typical composition for this alumina is 99.5 weight percent $Al_2O_3$, 0.10 weight percent $Na_2O$, 0.08 weight percent $SiO_2$, 0.04 weight percent $Fe_2O_3$, and 0.20 weight percent other volatiles. Total water content may be up to 0.3 weight percent.

The apparatus used for evaluating attrition on these small laboratory carrier preparations was constructed to specifically determine abrasion loss on very small amounts of material. The container for the test was a fibreboard tube with a metal bottom and screw-on metal cap. The outside height was 5¾ inch. Outside diameter was 2⅝ inch. A 1/16 inch thick silicon rubber pad was placed in the lid top and container bottom to completely cover the surfaces. The inside diameter of the tube was 2⅛ inch. The tube surface was covered with a ribbed rubber liner measuring 6⅝ inch by 5⅝ inch. Ribs of the rubber liner were made to run parallel to the tube axis. The end liners are glued into place but the ribbed liner is compressed in place without glue. Trimming of the inner liner was performed to make the edges fit flush on the end liners. The ribs of the inner liner were on ¼ inch centers and measured 3/32 inch at the base. Total rib height off the tube surface was 0.135 inch with the valley between the ribs 0.096 inch off the tube surface. Two strips of silicone rubber measuring 7⅞ inch by one inch by ⅛ inch were mounted on the outside ends of the tube for a roll surface. The container was rolled on a Norton Company roller mill to produce attrition which was measured at 5 minute intervals up to a total time of ½ hour. The procedure was to place 65 grams of carrier in the container and rotate the tube at 208 revolutions per minute and weigh the dust which fell through a 12 mesh screen each 5 minutes. Attrition was expressed as accumulative weight percent based on the original charge weight.

Crush strength was determined by testing at 0.5 inch per minute loading rate on a Comten Industries crush strength tester, Model No. 922-MV-05-OP. Median pore size and porosity determination were made by standard analysis on a Micrometrics porosimeter employing mercury intrusion.

EXAMPLE 1

The alumina powder was mixed with the additives employed and deionized water and thoroughly blended on a roller mill for ½ hour to obtain a uniform mixture. Spheres having a diameter of ¼ inch were then formed from the pasty mass, after which they were heated to 1500° C. for 10 hours. On cooling each batch was tested for physical properties and also compared with a similar batch (N) of a commercially prepared support without the barium aluminate.

Table I shows the amounts and kinds of additives used and Table II the resulting properties.

TABLE I

| Batch | Alumina (g) | M.C.* (g) | Cell.** (g) | Ba Aluminate (g) | $H_2O$ (g) |
|---|---|---|---|---|---|
| A | 98.0 | 2.0 | — | — | 30 |
| B | 97.3 | 2.0 | — | 0.7 | 30 |
| C | 88.0 | 2.0 | 10.0 | — | 8 |
| D | 87.3 | 2.0 | 10.0 | 0.7 | 8 |

*Hydroxypropylmethylcellulose (Methocel ® 60 HG - 50 cps @ 20° C.), a product of The Dow Chemical Company.
**Cellulose, a microcrystalline variety (Avicel ® PH 102) available from FMC Corp.

TABLE II

| Batch I.D. | Apparent Porosity (%) | Median Pore Size (μ) | Crush Strength (lb) | Attrition (Wt %) |
|---|---|---|---|---|
| A | 45 | 1.9 | 87 | 5.2 |

TABLE II-continued

| Batch I.D. | Apparent Porosity (%) | Median Pore Size (μ) | Crush Strength (lb) | Attrition (Wt %) |
|---|---|---|---|---|
| B | 42 | 2.2 | 146 | 4.0 |
| C | 48 | 5.6 | 14 | — |
| D | 49 | 5.6 | 39 | — |
| N | 50 | 8-10 | 30-40 | 2.0 |

Note that the crush strength was greatly increased when barium aluminate was added and the percent attrition was also decreased by over 20%.

EXAMPLE 2

Four carrier formulations were prepared to demonstrate the ability of barium aluminate to enhance the strength properties. All preparations were made in a sphere former which grows the beads in a rolling drum from a powder mix feed and deion water spray. The amount of water was adjusted to control the size of the beads to 3/16 inch diameter. A blend of 1000 grams of the same alumina used in Example 1 above and the additives was prepared for auger feeding to the sphere former. The blend was mixed on a roll mill for one hour prior to feeding. The product batches of the sphere former, were each split into four or five equal parts, each part to be fired at different temperatures and/or for different times.

The amounts and kinds of additives are shown in Table III and the firing conditions and resulting properties shown in Table IV.

TABLE III

| Batch | Alumina (g) | M.C.* (g) | Graphite** (g) | Ba Aluminate (g) |
|---|---|---|---|---|
| E | 1000 | 22.5 | — | — |
| F | 1000 | 22.6 | — | 7.2 |
| G | 1000 | 36.6 | 182.9 | — |
| H | 1000 | 36.9 | 184.5 | 8.6 |

*Same cellulose material used in Example 1 above.
**Grade 7101 graphite available from Asbury Graphite Mills, Inc.

TABLE IV

| Batch I.D. | Firing Conditions (°C./Hr) | Median Pore Diameter (μ) | Total Pore Volume (cc/g) | Crush Strength (lb) |
|---|---|---|---|---|
| E | 1500/1 | 2.2 | 0.199 | 45.5 |
|   | 1400/1 | — | — | 40.0 |
|   | 1500/10 | 2.5 | 0.199 | 59.1 |
|   | 1500/5 | 2.7 | 0.211 | 50.2 |
| F | 1500/1 | 2.9 | 0.206 | 49.4 |
|   | 1400/1 | — | — | 45.3 |
|   | 1500/10 | 3.0 | 0.210 | 64.9 |
|   | 1500/5 | — | — | 62.8 |
| G | 1550/1 | 5.7 | 0.270 | 22.6 |
|   | 1550/10 | — | — | 28.0 |
|   | 1500/10 | 5.9 | 0.299 | 20.6 |
|   | 1500/5 | — | — | 18.4 |
|   | 1500/1 | 7.6 | 0.274 | 14.2 |
| H | 1550/1 | 5.6 | 0.280 | 28.8 |
|   | 1550/10 | — | — | 37.6 |
|   | 1500/10 | 5.2 | 0.243 | 25.1 |
|   | 1500/5 | — | — | 23.8 |
|   | 1500/1 | 6.2 | 0.310 | 14.8 |

All the above support materials had surface area of between about 0.30 and 0.35 m²/g. It should be noted that all batches showed crush strength improvement with increased temperature and/or time while crush strengths at all firing temperatures and firing times improved with the addition of barium aluminate in the formulation. Comparison of batches "E" versus "F" and "G" versus "H" demonstrate the trend for strength improvement.

EXAMPLE 3

The invention was further tested by having supports made by a commercial manufacturer of catalyst support materials. Four different formulations numbered 1, 2, 3 and 4 were made up both with (A) and without (B) the addition of barium aluminate. The material was made into 3/16" diameter spheres and fired at temperatures and for times normally employed in their manufacturing operations.

Table V shows the physical properties of the support spheres resulting from these experiments. The abrasion loss was determined in the manner previously described except that the test container was larger in both length and diameter in order to contain a larger amount of catalyst. This test was conducted for 1 hour instead of a ½ hour.

TABLE V

| Sample No. | 1A | 1B | 2A | 2B | 3A | 3B | 4A | 4B |
|---|---|---|---|---|---|---|---|---|
| Surface area m²/g | 0.174 | 0.284 | 0.260 | 0.211 | 0.225 | 0.229 | 0.258 | 0.192 |
| Pore Volume, cc Hg/g | 0.385 | 0.458 | 0.388 | 0.467 | 0.360 | 0.309 | 0.342 | 0.440 |
| Median Pore Diam. μ | 14.0 | 7.0 | 10.7 | 7.4 | 9.3 | 6.9 | 11.3 | 9.0 |
| Crush, FPCS*, Lbs. | 52.0 | 21.3 | 36.5 | 26.9 | 63.9 | 63.1 | 46.9 | 37.8 |
| Abrasion, % loss | 2.4 | 15.8 | 4.4 | 11.6 | 2.2 | 10.4 | 2.8 | 12.8 |
| % Pore Distrib. | | | | | | | | |
| 1-10μ | 37.9 | 75.3 | 43.5 | 73.0 | 50.9 | 84.2 | 42.1 | 61.2 |
| 1-20μ | 68.0 | 89.1 | 76.4 | 88.7 | 83.9 | 90.9 | 74.8 | 90.4 |

*FPCS — flat plate crush strength

Each of the formulations were made with high purity alpha alumina which contains about 99.0 weight percent $Al_2O_3$ and minor amount of silica ($SiO_2$) and other metal oxides. Various additives to affect the pore size were employed. These catalyst supports were then used as carriers for silver in an ethylene oxide manufacturing process.

Samples of the modified supports were prepared as silver catalysts by the process of U.S. Pat. No. 4,248,741 for the purpose of testing in a small reactor. A volume of fifty cubic centimeters each of these several catalysts was tested in a one-half inch quartz glass tube reactor at a temperature sufficient to cause thirty percent of the ethylene fed to be converted to reaction products. An ethylene oxide selectivity based on ethylene converted was calculated.

The reaction conditions were
Pressure—20 in. $H_2O$
Space Velocity—540 $hr^{-1}$ The feed gas had the following % composition by volume
4.0% $C_2H_4$
6.0% $O_2$
7.5% $CO_2$
55-60 ppb Cl equivalent as inhibitor Balance $N_2$

EXAMPLE 4

Comparison experiments were run on silver catalysts prepared on various support formulations wherein barium had been incorporated as the aluminate (A) and as the silicate (S) and with no barium added (N). The amount of barium incorporated into the support, the temperature employed to obtain 30% ethylene conversion and the selectivity which resulted are shown. The amount of silver used on the support was 18% based on total catalyst weight. Results are found in Table VI.

TABLE VI

| Formulation | % Ba | Temperature (°C.) | Selectivity to EO (%) |
|---|---|---|---|
| 1N | 0 | 266 | 68.9 |
| 1A | 0.6 | 272 | 75.3 |
| 1S | 0.6 | 270 | 78.0 |
| 2N | 0 | 264 | 75.8 |
| 2A | 0.6 | 264 | 77.5 |
| 2S | 0.6 | 259 | 78.0 |
| 3N | 0 | 260 | 76.2 |
| 3A | 0.6 | 258 | 78.5 |
| 3S | 0.6 | 263 | 78.9 |
| 4N | 0 | 263 | 75.5 |
| 4A | 0.6 | 258 | 75.5 |
| 4S | 0.6 | 266 | 78.2 |

EXAMPLE 5

In order to determine whether additional barium incorporated as part of the catalytic surface had a beneficial effect, barium containing supports as in Example 4 had additional barium incorporated with the silver coating. The barium was added as the nitrate along with silver nitrate. The results of using these for oxidation of ethylene to ethylene oxide is shown in Table VII. The amount of silver loading was the same as in Example 4. All runs were made at 30% conversion. The A samples had barium aluminate and the S samples had the barium silicate incorporated into the support during manufacture as in Example 4.

TABLE VII

| Formulation | % Ba Added | Temp. (°C.) | Select. (%) |
|---|---|---|---|
| 1A | 0 | 272 | 75.3 |
| 1A | 0.10 | 279 | 74.1 |
| 1S | 0 | 270 | 78.0 |
| 1S | 0.10 | 269 | 77.8 |
| 2A | 0 | 264 | 77.5 |
| 2A | 0.10 | 259 | 77.6 |
| 2S | 0 | 259 | 78.0 |
| 2S | 0.10 | 266 | 78.5 |
| 3A | 0 | 258 | 78.5 |
| 3A | 0.10 | 265 | 77.1 |
| 3S | 0 | 263 | 78.9 |
| 3S | 0.10 | 268 | 77.4 |
| 4A | 0 | 258 | 75.5 |
| 4A | 0.10 | 270 | 75.0 |
| 4S | 0 | 266 | 78.2 |
| 4S | 0.10 | 273 | 77.8 |

From the above data it can be seen that additional barium on the surface had a deleterious effect on those catalysts made from supports having barium incorporated therein. Thus, so long as the barium, as the silicate or aluminate, is incorporated into the support, no added barium is needed on its surface and either has no effect or is counter-productive with respect to either activity or selectivity and in some cases both. Note that when barium was incorporated as a catalyst promoter on its surface, the support of Formulation 1S exhibited essentially no effect. In Formulation 2S, the selectivity was improved by adding the barium, but at the sacrifice of activity, i.e. the temperature required for 30% conversion was higher. In samples 1A, 3A, 4A, and 4S, both activity and selectivity were affected negatively.

EXAMPLE 6

The physical properties of supports containing barium silicate were obtained and compared with those in which no barium was added as with the aluminate comparison above. The B formulations are the same as in Table V. The properties are compared in Table VIII. The catalyst was made into 3/16 inch spheres as in Example 3.

TABLE VIII

| Sample No. | 1S | 1B | 2S | 2B | 3S | 3B | 4S | 4B |
|---|---|---|---|---|---|---|---|---|
| Surface area m²/g | 0.194 | 0.284 | 0.244 | 0.211 | 0.246 | 0.229 | 0.203 | 0.192 |
| Pore Volume, cc Hg/g | 0.417 | 0.458 | 0.409 | 0.467 | 0.410 | 0.309 | 0.397 | 0.440 |
| Median Pore Diam. μ | 12.9 | 7.0 | 11.9 | 7.4 | 13.2 | 6.9 | 11.5 | 9.0 |
| Crush, FPCS*, Lbs. | 77.4 | 21.3 | 67.9 | 26.9 | 69.8 | 63.1 | 83.0 | 37.8 |
| Abrasion, % loss | 2.6 | 15.8 | 4.2 | 11.6 | 2.6 | 10.4 | 2.8 | 12.8 |
| % Pore Distrib. | | | | | | | | |
| 1–10μ | 41.6 | 75.3 | 47.4 | 73.0 | 39.4 | 84.2 | 40.2 | 61.2 |
| 1–20μ | 84.9 | 89.1 | 84.6 | 88.7 | 72.5 | 90.9 | 69.1 | 90.4 |

*FPCS — flat plate crush strength

EXAMPLE 7

Larger amounts of Formulation 3A of Example III and Table V containing 1.0% by weight barium aluminate were prepared and two other batches of the same formulation containing different amounts of the barium component were prepared using 0.4 and 0.7% barium aluminate. Large batches of Formulation 1A were likewise prepared except that only amounts of 0.4 and 0.7% were used. The results of physical tests are shown in Table IX.

TABLE IX

| Sample No. | 3A | 5A | 6A | 7A | 8A |
|---|---|---|---|---|---|
| % Ba Aluminate Added | 1.0 | 0.7 | 0.4 | 0.7 | 0.4 |
| Surface area, m²/g | 0.234 | 0.240 | 0.251 | 0.192 | 0.156 |
| Pore Volume, cc Hg/g | 0.340 | 0.347 | 0.351 | 0.386 | 0.346 |
| Median Pore Diam., μ | 7.0 | 6.3 | 5.6 | 11.8 | 12.2 |
| Crush, FPCS*, lbs. | 60.6 | 67.8 | 61.0 | 77.0 | 72.9 |
| Abrasion, % loss | 5.0 | 4.4 | 5.0 | 3.0 | 2.2 |
| % Pore Distrib. | | | | | |
| 1–10μ | 71.5 | 74.3 | 75.8 | 41.5 | 41.2 |
| 1–20μ | 84.4 | 89.4 | 86.0 | 79.5 | 75.4 |

*FPCS — flat plate crush strength

EXAMPLE 8

The supports of Example 7 were employed as silver catalysts (18% Ag) in the preparation of EO using a feed gas containing 6.0 mole % $C_2H_4$, 6.2 mole % $O_2$, and 7-15 ppb equivalent Cl in EDC as an inhibitor. A volume of the catalyst was loaded into a testing reactor having a 1½ inch diameter reaction tube twenty feet in length. A preheater brought the synthetic feed mixture to a temperature of 220° C. before entering the reactor. The reaction pressure was 250 psig. Each catalyst was run at a temperature sufficient to cause 1.55 mole percent ethylene to be converted to reaction products. This results in about 25.8% conversion of the ethylene. Results are shown in Table X.

TABLE X

| Formulation | % Ba Aluminate Added | Temperature | Selectivity |
|---|---|---|---|
| 3A | 1.0 | 253° C. | 69.6 |
| 5A | 0.7 | 256° C. | 71.2 |
| 7A | 0.7 | 256° C. | 73.9 |
| 8A | 0.4 | 258° C. | 73.0 |

I claim:

1. A high purity alumina low surface area catalyst support having improved crush strength and abrasion resistance comprising alumina and barium aluminate or barium silicate, wherein said barium aluminate or silicate is uniformly distributed as a binder and is present in an amount sufficient to provide from about 0.1% to about 1.0% by weight barium in the finished support.

2. The catalyst support of claim 1 wherein the alumina has a purity of about $\geq 99.0\%$ $Al_2O_3$.

3. The catalyst support of claim 2 wherein the support is in a spherical form.

4. A process for making high purity alumina support which comprises
    (A) mixing together
    (1) high purity alumina powder,
    (2) barium aluminate or silica powder,
    (3) a pore-forming organic material and
    (4) water in sufficient quantity to make a paste;
    (B) forming said paste into support form;
    (C) heating said support form at a temperature within the range of about 1200° to 1700° C. to form a crush resistant and abrasion resistant catalyst support.

5. The process of claim 4 wherein the alumina has a purity of about $\geq 99.0\%$.

6. The process of claim 5 wherein the pore-forming material is cellulose or an alkylated or hydroxyalkylated cellulose.

7. The process of claim 6 wherein the alkylated cellulose is methyl- or ethylcellulose.

8. The process of claim 6 wherein the hydroxyalkylated cellulose is hydroxypropyl- or hydroxybutylmethylcellulose.

9. The process of claim 5 wherein the pore-forming material is graphite.

10. The process of claims 4, 5, 6, 7, 8 or 9 wherein the pore-forming material is present in an amount of from about 2 to about 20% based on the total weight of the dry components.

11. The process of claims 4, 5, 6, 7, 8 or 9 wherein the alumina is present in an amount of from about 99.84 to about 98.1% and the barium compound is present in an amount of from about 0.16 to about 1.9% based on the total weight of the alumina and barium compound.

12. A silver catalyst comprising a coating of silver metal on a high purity alumina support wherein said support contains alumina and barium aluminate or barium silicate, said barium aluminate or silicate being uniformly distributed as a binder and is present in an amount sufficient to provide from about 0.1 to about 1.0% by weight barium in the finished support.

13. The catalyst of claim 10 wherein the silver coating comprises from about 5 to about 20% of the total weight of the catalyst.

* * * * *

UNITED STATES PATENT AND TRADEMARK OFFICE
CERTIFICATE OF CORRECTION

PATENT NO. : 4,428,863
DATED : January 31, 1984
INVENTOR(S) : William E. Fry

It is certified that error appears in the above—identified patent and that said Letters Patent is hereby corrected as shown below:

Col. 2, lines 55-56; delete "bind- ers in making a high purity low surface area alumina".

Col. 10, line 2; delete "silica" and insert therefore --silicate--.

Signed and Sealed this

Thirty-first Day of July 1984

[SEAL]

Attest:

GERALD J. MOSSINGHOFF

Attesting Officer

Commissioner of Patents and Trademarks